United States Patent
Wahlstrand et al.

(10) Patent No.: US 7,389,147 B2
(45) Date of Patent: Jun. 17, 2008

(54) THERAPY DELIVERY MODE SELECTION

(75) Inventors: Carl D. Wahlstrand, Lino Lakes, MN (US); Robert M. Skime, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 166 days.

(21) Appl. No.: 11/119,420

(22) Filed: Apr. 29, 2005

(65) Prior Publication Data

US 2006/0247739 A1    Nov. 2, 2006

(51) Int. Cl.
*A61N 1/00* (2006.01)

(52) U.S. Cl. .............................. 607/60; 607/64

(58) Field of Classification Search ................. 607/60, 607/64

See application file for complete search history.

(56) References Cited

U.S. PATENT DOCUMENTS

| | | | |
|---|---|---|---|
| 5,342,404 A | 8/1994 | Alt et al. | |
| 5,593,431 A * | 1/1997 | Sheldon | 607/19 |
| 5,628,317 A | 5/1997 | Starkebaum et al. | |
| 5,814,092 A | 9/1998 | King | |
| 5,836,983 A * | 11/1998 | Weijand et al. | 607/9 |
| 5,941,906 A | 8/1999 | Barreras, Sr. et al. | |
| 6,032,674 A | 3/2000 | Eggers et al. | |
| 6,319,241 B1 | 11/2001 | King et al. | |
| 6,393,325 B1 * | 5/2002 | Mann et al. | 607/46 |
| 6,795,737 B2 | 9/2004 | Gielen et al. | |
| 7,139,608 B2 | 11/2006 | Ideker et al. | |

(Continued)

FOREIGN PATENT DOCUMENTS

EP    0 547 482 A1    6/1993

(Continued)

OTHER PUBLICATIONS

International Search Report and Written Opinion dated Oct. 10, 2006 for corresponding PCT Application No. PCT/US2006/014190, filed Apr. 12, 2006 (12 pgs.).

(Continued)

*Primary Examiner*—Carl H. Layno
*Assistant Examiner*—Brian T Gedeon
(74) *Attorney, Agent, or Firm*—Shumaker & Sieffert, P.A.

(57) ABSTRACT

Techniques for selectably providing either constant voltage or constant current stimulation are described. A programming device provides a user interface by which a user selects either constant voltage or constant current stimulation, and selects either a voltage or current amplitude based on the selected stimulation mode. The programming device configures a medical device to provide the selected mode of stimulation at the selected amplitude. For example, when a medical device has constant voltage stimulation circuitry, e.g., circuitry including a voltage source, and the user selects constant current stimulation, the programming device configures the medical device to adjust the voltage amplitude based on a measured impedance to provide substantially constant current amplitude.

12 Claims, 8 Drawing Sheets

U.S. PATENT DOCUMENTS

| | | | |
|---|---|---|---|
| 2001/0053885 A1 | 12/2001 | Gielen et al. | |
| 2004/0024421 A1 | 2/2004 | Ideker et al. | |
| 2004/0102712 A1 | 5/2004 | Belalcazar et al. | |
| 2004/0116784 A1 | 6/2004 | Gavish | |
| 2004/0122486 A1* | 6/2004 | Stahmann et al. | 607/60 |
| 2004/0220637 A1 | 11/2004 | Zdeblick et al. | |
| 2004/0254483 A1 | 12/2004 | Zbeblick et al. | |
| 2006/0247732 A1* | 11/2006 | Wesselink | 607/46 |
| 2007/0055315 A1 | 3/2007 | Ideker et al. | |
| 2007/0156206 A1* | 7/2007 | Wahlstrand et al. | 607/62 |

FOREIGN PATENT DOCUMENTS

EP    0 904 739 A2    3/1999

OTHER PUBLICATIONS

E. Dijkstra, *Ultrasonic distance detection for spinal cord stimulation*, Ph.D. Thesis, Chapter 6, pp. 116-117 (2003).

Holsheimer J and Wesselink WA, Neurosurgery, *Effect of Anode-Cathode Configuration on Paresthesia Coverage in Spinal Cord Stimulation*, vol. 41, No. 3, pp. 654-660 (Sep. 1997).

Notification of Transmittal of the International Preliminary Report on Patentability dated Apr. 20, 2007 for corresponding PCT Application No. PCT/US2006/014190, filed Apr. 12, 2006 (8 pgs.).

* cited by examiner

THERAPY DELIVERY MODE SELECTION

TECHNICAL FIELD

The invention is directed to medical devices and, more particularly, medical devices that deliver electrical stimulation.

BACKGROUND

Medical devices deliver electrical stimulation in order treat a variety of ailments or symptoms of patients, such as pain, epilepsy, and movement disorders. Often, the medical devices used to treat such ailments or symptoms are implantable. Further, whether implanted or not, the medical devices often deliver stimulation to tissue via one or more conductors within a lead, which may include one or more lead extensions, and the electrodes associated with these conductors that are carried by the lead.

Over the life of the medical device, the impedance presented to the medical device by the conductors, electrodes, and tissue proximate to the electrodes, e.g., the impedance of the conductors, electrodes, and tissue, may vary. This variation in presented impedance may be due to a variety of factors, such as lead material degradation, changes in patient hydration, and changes in the type of tissue proximate to the electrodes, which may be due to, for example, movement of the electrodes relative to the tissue intended to be stimulated, or growth of tissue at the stimulation site. When the patient is active, e.g., moving and/or changing postures, the electrodes may move relative to the tissue intended to be stimulated.

Medical devices that deliver electrical stimulation generally fall into one of two categories. Constant voltage devices include a voltage source, such as a voltage regulator, that outputs the stimulation at a specified voltage amplitude, while constant current devices include a current source, such as a current mirror, that outputs the stimulation at a specified current amplitude. These voltage and current sources hold their stimulation at a constant voltage or current amplitude, respectively. However, due to changes in the presented impedance over time, the current output by a constant voltage device, and the voltage output by a constant current device, will vary.

Clinicians may prefer either a constant voltage or constant current device for any of a variety reasons. For example, some clinicians prefer one of these types of devices for a particular therapy. Others may prefer one of these types of devices due to familiarity, or for other idiosyncratic reasons.

SUMMARY

In general, the invention is directed to techniques and devices for selectably providing either constant voltage or constant current stimulation. A programming device provides a user interface by which a user selects either constant voltage or constant current stimulation, and either a voltage or current amplitude based on the selected stimulation mode. The programming device configures a medical device to provide the selected mode of stimulation at the selected amplitude. In this manner, a user, such as a clinician, may configure a medical device to provide the mode of stimulation that they prefer.

According to the invention, a constant voltage medical device may deliver stimulation with a substantially constant current amplitude by adjusting a voltage amplitude of the stimulation based on a measurement of the impedance presented to the medical device. Similarly, a constant current medical device may deliver a substantially constant voltage by adjusting a current amplitude of the stimulation based on the presented impedance. A medical device may periodically measure the presented impedance to determine the adjustments to the voltage or current stimulation amplitude.

In some embodiments, a medical device senses patient activity, e.g., motion, footfalls, and/or posture changes, and determines a "measurement frequency" based on the sensed activity. A "measurement frequency" pertains to how often the medical device makes a measurement of the presented impedance. The presented impedance may change more frequently when a patient is active, e.g., moving and/or changing postures. Consequently, the medical device may select a higher measurement frequency as patient activity increases, and a lower measurement frequency as patient activity decreases. The medical device also adjusts the stimulation amplitude based on the measured impedances. Consequently, the medical device may also adjust the stimulation amplitude at a frequency that is based on patient activity. In this manner, the voltage or current amplitude adjustments may be able to more effectively track rapid impedance changes to maintain a substantially constant current or voltage amplitude. The impedance measurement frequency determination may be based on comparison of the sensed patient activity to one or more thresholds, functions, look-up tables, or the like, that define a relationship between measurement frequency and activity. Such information defining a relationship between measurement frequency and activity may be stored by the medical device and, in some embodiments, received from a user via a programming device.

In one embodiment, the invention is directed to a programming device comprising a user interface and a processor. The processor prompts a user for selection of one of a constant current mode or a constant voltage mode via the user interface, receives a selection of one of the modes from the user via the user interface, and configures a medical device according to the selected mode.

In another embodiments, the invention is directed to a method that comprises prompting a user for selection of one of a constant current mode or a constant voltage mode, receiving a selection of one of the modes from the user, and configuring a medical device according to the selected mode.

In another embodiment, the invention is directed to a computer-readable medium comprising instructions. The instructions cause a programmable processor to prompt a user for selection of one of a constant current mode or a constant voltage mode, receive a selection of one of the modes from the user, and configure a medical device according to the selected mode.

In another embodiment, the invention is directed to a medical device comprising stimulation circuitry configured to deliver one of constant voltage or constant current stimulation, an activity sensor to sense patient activity, an impedance measurement circuit for measuring an impedance presented to the stimulation circuitry, and a processor to determine a measurement frequency based on the sensed patient activity, control the impedance measurement circuit to measure the impedance at the determined measurement frequency, and adjust an amplitude of the stimulation based on the measured impedance to substantially provide the other of constant voltage or constant current stimulation.

In another embodiment, the invention is directed to a method that comprises sensing patient activity, determining a measurement frequency based on the sensed activity, measuring the impedance presented to stimulation circuitry of a medical device at the determined frequency, wherein the stimulation circuitry is configured to deliver one of constant voltage or constant current stimulation, and adjusting an amplitude of the stimulation based on the measured impedance to substantially provide the other of constant voltage or constant current stimulation.

In another embodiment, the invention is directed to a medical device comprising means for sensing patient activity, means for determining a measurement frequency based on the sensed activity, means for measuring the impedance presented to stimulation circuitry of a medical device at the determined frequency, wherein the stimulation circuitry is configured to deliver one of constant voltage or constant current stimulation, and means for adjusting an amplitude of the stimulation based on the measured impedance to substantially provide the other of constant voltage or constant current stimulation.

Embodiments of the invention may be capable of providing advantages. For example, embodiments of the invention may allow a user, such as a clinician, to configure a medical device to provide the mode of stimulation that they prefer. Additionally, changing the frequency of the impedance measurements based on patient activity may allow a medical device according to the invention to deliver stimulation with a substantially constant current or voltage amplitude, as desired, while avoiding unnecessary consumption of a medical device power source and/or unnecessary diversion of stimulation energy for the purposes of the presented impedance measurements.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
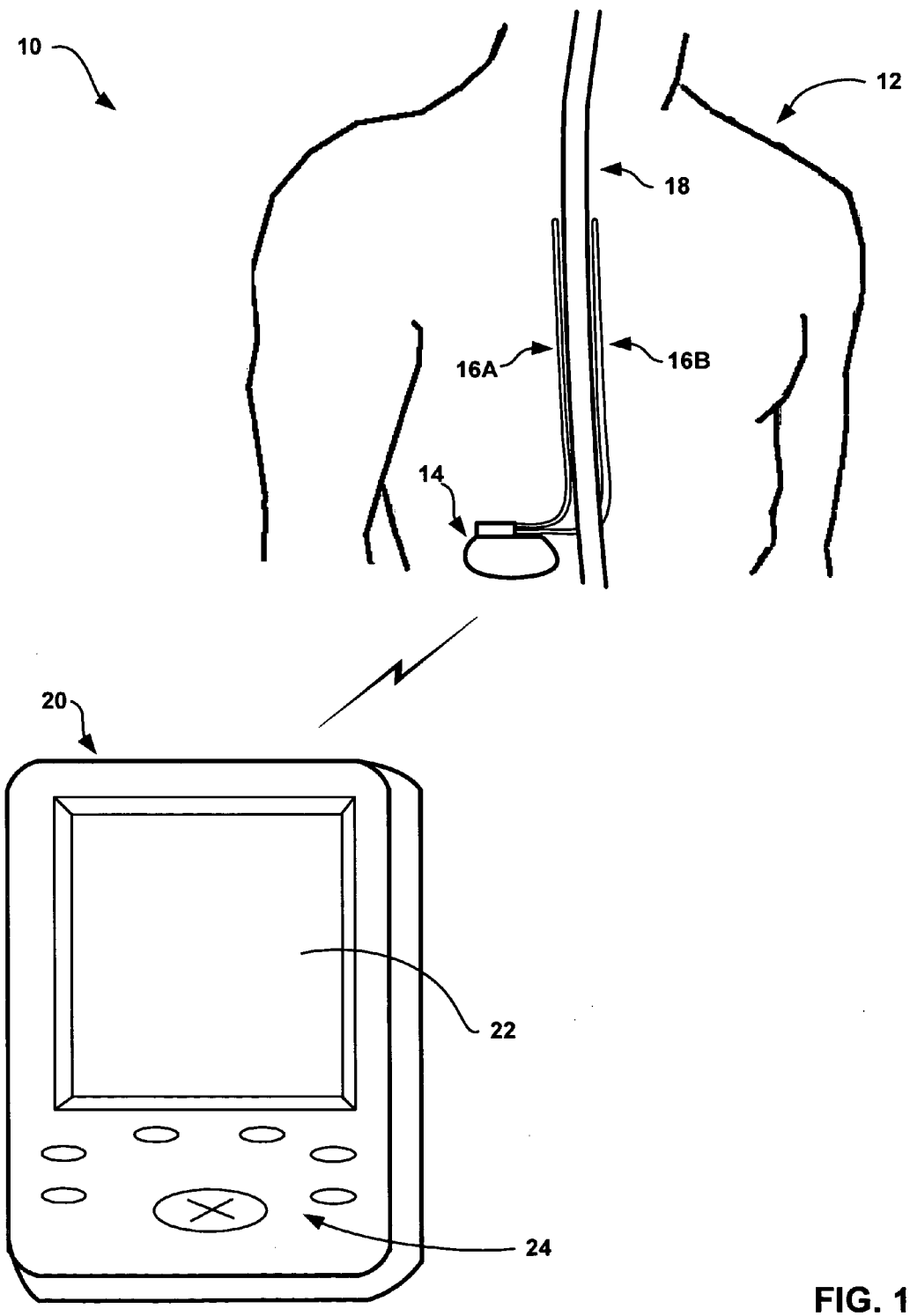
FIG. 1 is a conceptual diagram illustrating an example system, including an implantable medical device that selectably provides constant voltage or constant current stimulation, in conjunction with a programming device and a patient.

FIG. 1 is a conceptual diagram illustrating an example system 10, including an implantable medical device (IMD) 14. As will be described in greater detail below, IMD 14 is selectably configurable to deliver either constant voltage or constant current stimulation. A user, such as a clinician, may configure IMD 14 to provide the mode of stimulation that the user prefers.

In the illustrated example system 10, IMD 14 takes the form of an implantable neurostimulator that delivers stimulation in the form of electrical pulses to patient 12. However, the invention is not limited to implementation via an implantable neurostimulator. For example, in some embodiments of the invention, implantable cardiac rhythm management device, such as a pacemaker, may selectably provide either constant current or constant voltage stimulation. Further, the invention is not limited to implementation via an IMD, or a medical device that delivers stimulation in the form of electrical pulses. In other words, any implantable or external medical device that delivers stimulation may be configurable to deliver either constant voltage or constant current stimulation in accordance with the invention.

In the example of FIG. 1, IMD 14 delivers stimulation to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) or cortical stimulation to patient 12 to, for example, treat tremor or epilepsy. As further examples, one or more leads 16 may be implanted proximate to the pelvic nerves (not shown) or stomach (not shown), and IMD 14 may deliver stimulation to treat incontinence, gastroparesis, or sexual dysfunction. The implantation location of IMD 14 is merely exemplary.

IMD 14 may be either a constant voltage device, meaning that IMD 14 includes a voltage source for delivery of stimulation, or a constant current device, meaning that IMD 14 includes a current source for delivery of stimulation. The voltage or current source of IMD 14 may be controlled to deliver stimulation at a selected voltage or current amplitude, and with selected values for other characteristics, such as pulse width and rate. In general, constant voltage IMDs control their voltage sources to provide a constant voltage output by holding the output voltage amplitude at a fixed value until changed to a new value by a user or software. Similarly, constant current IMDs typically control their current sources to provide a constant current output by holding the output current amplitude at a fixed value until changed to a new value by a user or software. However, due to variations in the impedance presented to such IMDs, the amplitude of the current output by a constant voltage device, or the voltage output by a constant current device, would vary.

According to the invention, an IMD 14, which may be either a constant current IMD or a constant voltage IMD, may be configured to deliver either constant voltage or constant current stimulation. As will be described in greater detail below, a constant voltage IMD 14 may deliver constant current stimulation by measuring the impedance presented to the IMD, and adjusting the voltage amplitude output by its voltage source based on the measured impedance such that the current amplitude of the stimulation is substantially constant. Similarly, a constant current IMD 14 may deliver constant voltage stimulation by measuring the impedance presented to the IMD, and adjusting the current amplitude output by its current source based on the measured impedance such that the voltage amplitude of the stimulation is substantially constant.

The presented impedance may include the impedance presented by electrodes, conductors within leads and extensions associated with the electrodes, and tissue proximate to the electrodes. As described above, the presented impedance may vary due to a variety of factors, such as lead material degradation, changes in patient hydration, and changes in the type of tissue proximate to the electrodes, which may be due to, for example, movement of the electrodes relative to the tissue intended to be stimulated, or growth of tissue at the stimulation site. When the patient is active, e.g., moving and/or changing postures, the electrodes may move relative to the tissue intended to be stimulated.

As shown in FIG. 1, system 10 also includes a programming device 20. A clinician, for example, may use programming device 20 to program therapy for patient 12, e.g., specify a number of parameters of the stimulation delivered by IMD 14, such as pulse amplitude, width, rate, and electrode polarity. The clinician may also use programming device 20 to retrieve information collected by IMD 14. The clinician may use programming device 20 to communicate with IMD 14 both during initial programming of IMD 14, and for collection of information and further programming during follow-up visits. Further, as will be described in greater detail below, a clinician my use programming device 20, based on the clinician's preference, to configure IMD 14 to deliver either constant voltage or constant current stimulation.

Programming device 20 may, as shown in FIG. 1, be a handheld computing device. Programming device 20 includes a display 22, such as a LCD or LED display, to display information to a user. Programming device 20 may also include a keypad 24, which may be used by a user to interact with the programming device. In some embodiments, display 22 may be a touch screen display, and a user may interact with programming device 20 via display 22. A user may also interact with programming device 20 using peripheral pointing devices, such as a stylus or mouse. Keypad 24 may take the form of an alphanumeric keypad or a reduced set of keys associated with particular functions.

However, programming device 20 is not limited to the hand-held computer embodiments illustrated in FIG. 1. Programming devices 20 according to the invention may be any sort of computing device. For example, a programming device 20 according to the invention may be a tablet-based computing device, a desktop computing device, or a workstation. Programming device 20 may communicate with IMD 14 via wireless communication using radio frequency (RF) telemetry techniques known in the art.

Figure 2:
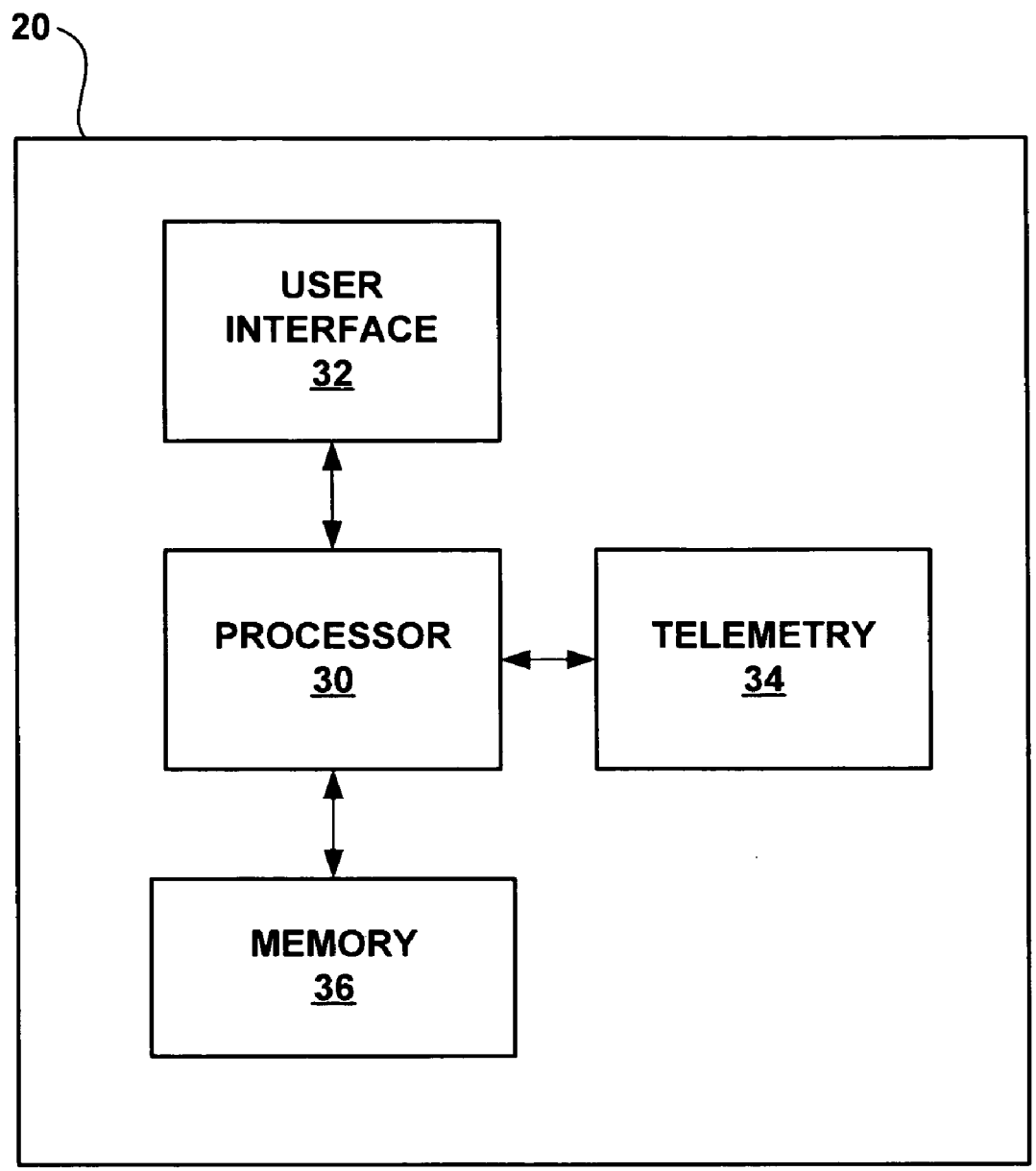
FIG. 2 is functional block diagram further illustrating the programming device of FIG. 1.

FIG. 2 is functional block diagram further illustrating programming device 20. A user, such as a clinician, may interact with a processor 30 via a user interface 32 in order to select either constant voltage or constant current stimulation, and to program therapy for patient 12. Processor 30 configures IMD 14 through communication via telemetry circuitry 34. User interface 32 may include display 22 and keypad 24, and may also include a touch screen or peripheral pointing devices as described above. Processor 30 may include any one or more of a microprocessor, a controller, a digital signal processor (DSP), an application specific integrated circuit (ASIC), a field-programmable gate array (FPGA), discrete logic circuitry, or the like.

Programming device 20 also includes a memory 36. Memory 36 may store program instructions that, when executed by processor 30, cause programming device 20 to perform the functions ascribed to programming device 20 herein. Memory 36 may include any volatile, non-volatile, fixed, removable, magnetic, optical, or electrical media, such as a random access memory (RAM), read-only memory (ROM), CD-ROM, hard disk, removable magnetic disk, memory cards or sticks, non-volatile RAM (NVRAM), electronically erasable programmable ROM (EEPROM), flash memory, and the like.

Figure 3:
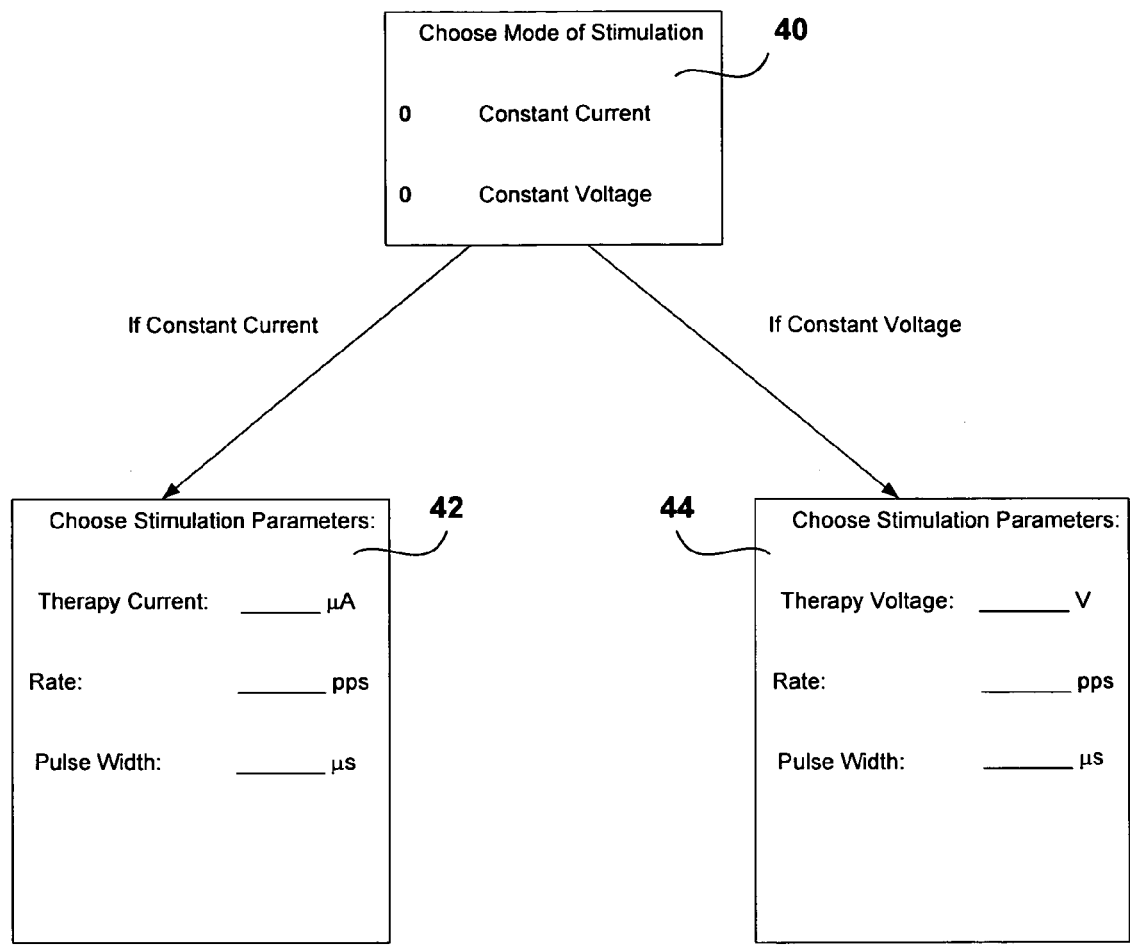
FIG. 3 is flow diagram illustrating screens displayed by a programming device according to an example embodiment.

FIG. 3 is flow diagram illustrating example screens 40, 42 and 44 that may be displayed to a user by programming device 20. In particular, processor 30 may cause screens 40, 42 and 44 to be presented via user interface 32, e.g., via display 22. As illustrated by screen 40, a user may be prompted to select one of constant current or constant voltage stimulation.

If the user selects constant current stimulation, processor 30 may present screen 42 via display 22. Via screen 42, the user selects values for stimulation parameters and, notably, selects a current amplitude for the stimulation. A user who prefers and selects constant current stimulation will likely prefer selecting a current, as opposed to voltage, amplitude.

If the user selects constant voltage stimulation, processor 30 may present screen 44 via display 22. Via screen 44, the user selects values for stimulation parameters and, notably, selects a voltage amplitude for the stimulation. A user who prefers and selects constant voltage stimulation will likely prefer selecting a voltage, as opposed to current, amplitude.

Figure 4:
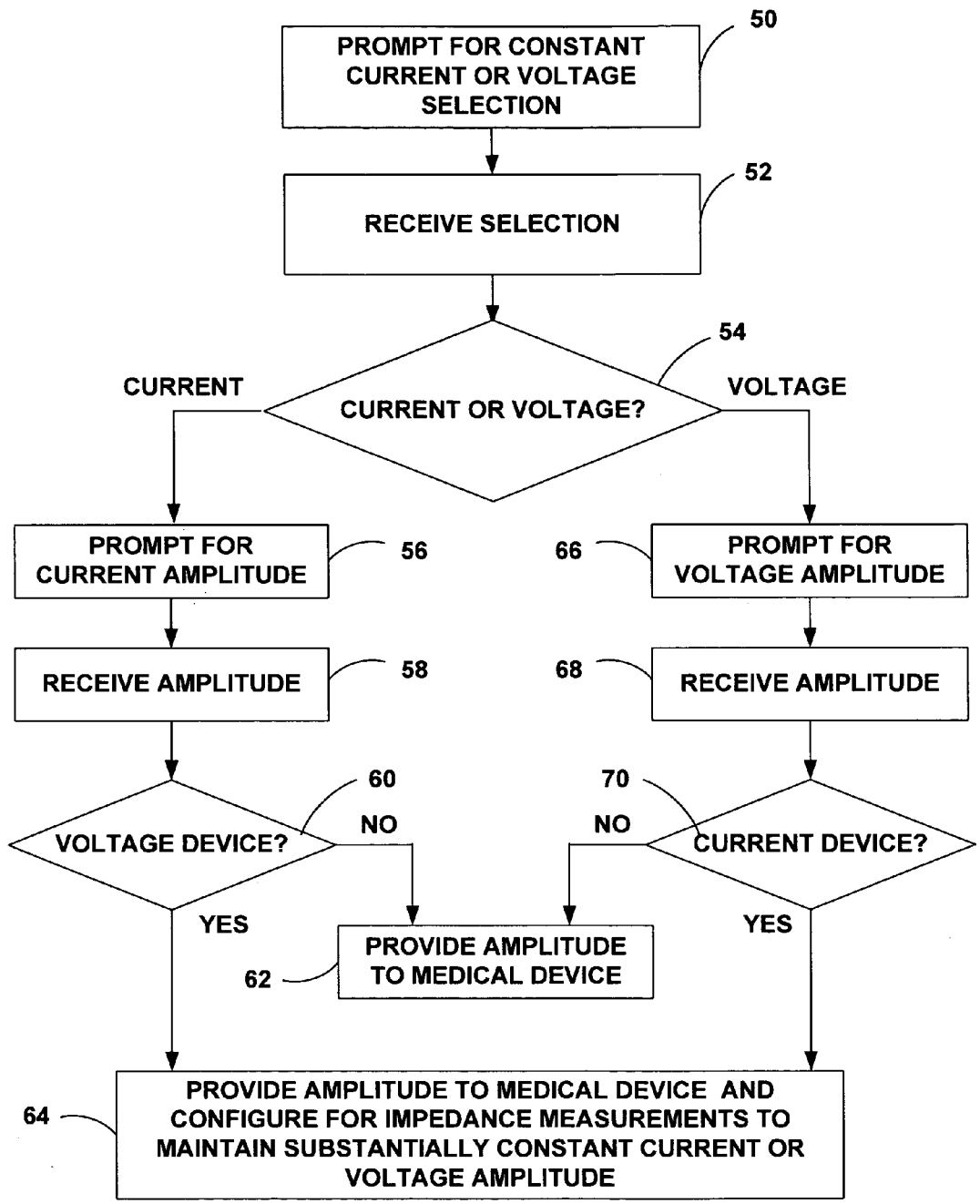
FIG. 4 is a flow diagram illustrating an example method for configuring a medical device for either constant voltage or current stimulation.

FIG. 4 is a flow diagram illustrating an example method for configuring a medical device for either constant voltage or current stimulation that may be performed by programming device 20. According to the example method, programming device 20, and more particularly processor 30 of programming device 20, prompts a user to select either a constant current or constant voltage stimulation mode via user interface 32, e.g., display 22 (50), and receives the selection from the user via the user interface, e.g., keypad 24 (52).

If the user selects the constant current stimulation mode (54), processor 30 prompts the user for a current amplitude value via user interface 32 (56). Processor 30 receives the current amplitude value from the user via the user interface (58). If the medical device is a constant current device (60), processor 30 provides the current amplitude value to the medical device, e.g., via telemetry circuitry 34 (62). If the medical device is a constant voltage device (60), processor 30 provides the current amplitude value to the medical device, and configures the medical device such that it will perform impedance measurements and stimulation voltage amplitude adjustments to maintain the stimulation current amplitude substantially at the specified current amplitude value (64).

If the user selects the constant voltage stimulation mode (54), processor 30 prompts the user for a voltage amplitude value via user interface 32 (66). Processor 30 receives the voltage amplitude value from the user via the user interface (68). If the medical device is a constant voltage device (70), processor 30 provides the voltage amplitude value to the medical device, e.g., via telemetry circuitry 34 (62). If the medical device is a constant current device (70), processor 30 provides the voltage amplitude value to the medical device, and configures the medical device such that it will perform impedance measurements and stimulation current amplitude adjustments to maintain the stimulation voltage amplitude substantially at the specified voltage amplitude value (64).

Figure 5:
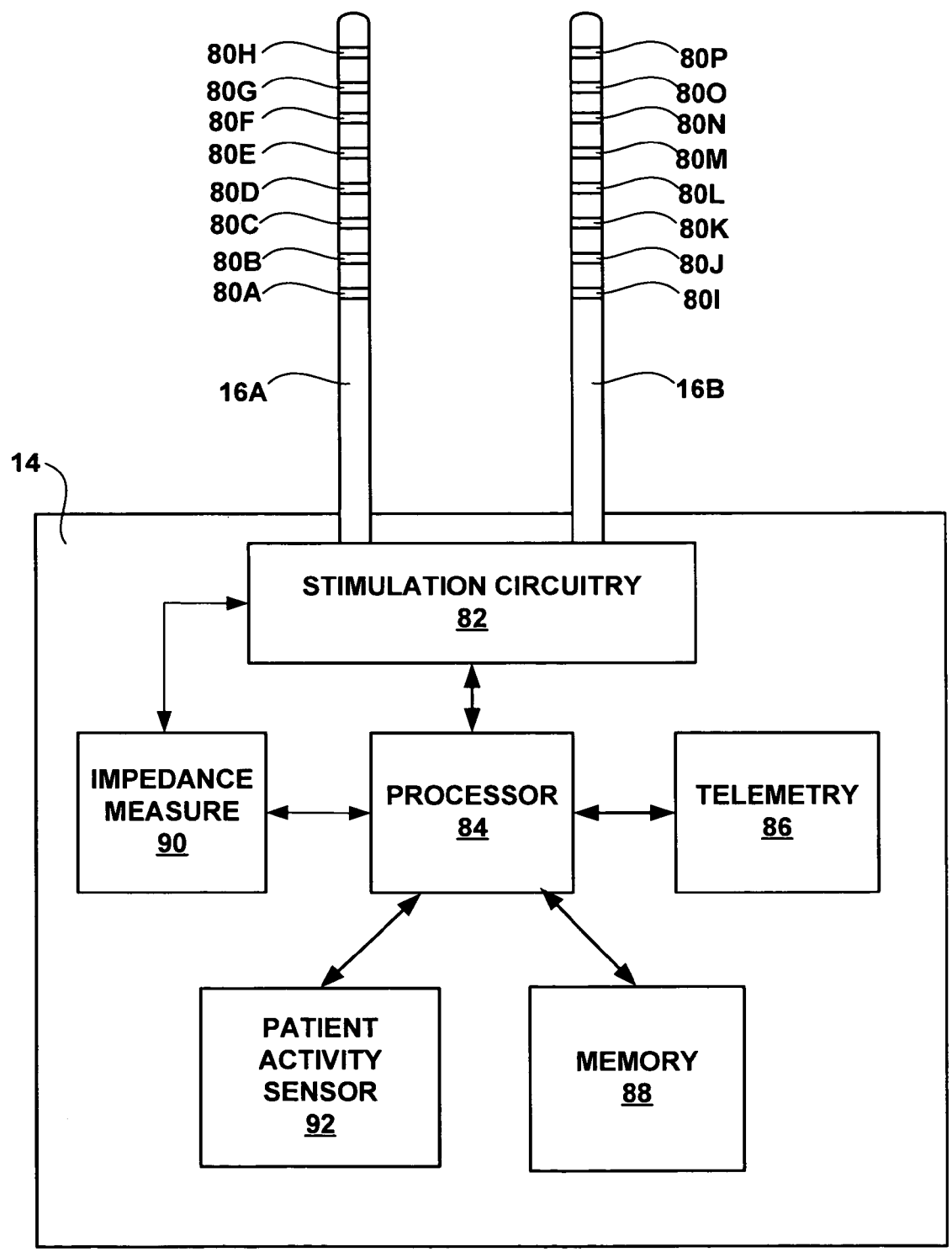
FIG. 5 is a functional block diagram further illustrating the implantable medical device of FIG. 1.

FIG. 5 is a functional block diagram further illustrating IMD 14 coupled to leads 16. IMD 14 may deliver stimulation to a selected one or more of electrodes 80A-H of lead 16A and electrodes 80I-P of lead 16B (collectively "electrodes 80"). Electrodes 80 may be ring electrodes. The configuration, type and number of electrodes 80 illustrated in FIG. 5 are exemplary. For example, leads 16A and 16B may each include fewer than eight electrodes 80, and the electrodes 80 need not be arranged linearly on each of leads 16A and 16B.

Electrodes 80 are electrically coupled to stimulation circuitry 82 via respective conductors within leads 16. Under the control of a processor 84, stimulation circuitry 82 generates electrical stimulation for delivery to patient 12 via electrodes 80. As discussed above, one or more electrodes 80, their respective conductors, and tissue of patient 12 proximate to the electrodes presents an impedance to stimulation circuitry 82.

Stimulation circuitry 82 may be either constant current or constant voltage stimulation circuitry. Constant current stimulation circuitry includes one or more current sources, such as one or more current mirrors, while constant voltage stimulation circuitry contains one or more voltages sources, such as one or more voltage regulators. Processor 84 controls stimulation circuitry 82 to deliver stimulation with selected values for parameters such as pulse amplitude, width and rate. Processor 84 also controls coupling of, e.g., switches that couple, selected electrodes 80 to stimulation circuitry 82. Processor 84 may receive the values for such stimulation parameters from programming device 20 via telemetry circuitry 86, and store such values in a memory 88.

Processor 84 may also receive an indication whether IMD 14 is to deliver constant current or voltage stimulation from programming device 20 via telemetry circuitry 86. If IMD 14 is a constant current device directed to deliver constant voltage stimulation, or a constant voltage device directed to deliver constant current stimulation, processor will periodically control impedance measurement circuitry 90 to measure the impedance presented to stimulation circuitry 82. Based on the measured impedance, processor adjusts the current amplitude of stimulation generated by constant current stimulation circuitry to provide substantially constant stimulation voltage, or the voltage amplitude of stimulation generated by constant voltage stimulation circuitry to provide a substantially constant stimulation current.

Impedance measurement circuitry 90 may include resistors, capacitors, or other known circuitry that may be coupled in series or parallel with stimulation circuitry 82 for measurement of one or both of voltage or current when an electrical signal is delivered by the stimulation circuitry. Processor 84 may determine the impedance based on the measured voltage and/or current. Equations or the like used by processor 84 to determine the lead impedance may be stored in memory 88.

Processor 84 may control stimulation circuitry 82 to deliver a dedicated, e.g., subthreshold, signal, and control impedance measurement circuitry 90 to measure the impedance during the delivery. More preferably, processor 84 controls impedance measurement circuitry 90 to measure the impedance during delivery of therapeutic stimulation to patient 12 by stimulation circuitry 82. Processor 84 periodically controls impedance measurement circuitry 90 to measure the impedance, and the frequency of measurements may be significantly less than that of the stimulation, e.g., less than the pulse rate. For example, the measurement frequency may be on the order of one measurement every one or more minutes, hours, or days. On the other hand, the measurement frequency may be on the order of one measurement occurring every one or more stimulation pulses.

As shown in FIG. 5, IMD 14 may include a patient activity sensor 92. Patient activity sensor 92 may include any sensor that generates a signal as a function of patient activity, such as one or more of an accelerometer, a piezoelectric element, a mercury switch, electromyogram (EMG) electrodes, or electrocardiogram (ECG) electrodes. Sensors 92 may generate a signal as a function of gross muscle movement, footfalls, and/or posture.

Changes in the impedance presented to stimulation circuitry 82 may be particular large when the activity of patient 12 includes posture changes. A plurality of orthogonally aligned sensors 92, such as accelerometers, mercury switches, gyros, or magnetometers, may generate signals that indicate patient posture. In addition to being oriented orthogonally with respect to each other, each of sensors 92 used to detect the posture of patient 12 may be generally aligned with an axis of the body of patient 12. In exemplary embodiments, IMD 14 includes three orthogonally oriented sensors 92.

When sensors 92 include accelerometers, for example, that are aligned in this manner, processor 84 may monitor the magnitude and polarity of DC components of the signals generated by the accelerometers to determine the orientation of patient 12 relative to the Earth's gravity, e.g., the posture of patient 12, and identify when and how often the posture changes. Further information regarding use of orthogonally aligned accelerometers to determine patient posture may be found in a commonly assigned U.S. Pat. No. 5,593,431, which issued to Todd J. Sheldon. An example sensor 92 that may be used to detect patient activity, including posture changes, is an Inertial Sensor: 3Axis—2g/6g Linear Accelerometer, commercially available from STMicroelectronics. Sensor 92 may be included within IMD 14, or coupled to IMD 14 wirelessly or by a lead.

In some embodiments, the impedance measurement frequency is variable. For example, because the presented impedance is likely to change more frequently during periods when the patient is active, e.g., moving or changing postures, it may be desirable to measure impedance and adjust stimulation amplitude more frequently when patient 12 is active. Processor 84 may determine an activity level of patient 12 based on a signal from patient activity monitor 92, and determine an impedance measurement frequency based on the activity level. For example, processor 84 may compare the activity level to information defining a relationship between patient activity and measurement frequency, e.g., one or more threshold values, look-up tables, or equations, stored in memory to determine the measurement frequency. Such information may be received from or modified by a user via programming device 20. The activity levels determined by processor 84 may be averages over a period of time, such as several seconds or minutes.

Processor 84 may include a microprocessor, a controller, a DSP, an ASIC, an FPGA, discrete logic circuitry, or the like. Memory 88 may include any volatile, non-volatile, magnetic or electrical media, such as a RAM, ROM, NVRAM, EEPROM, flash memory, and the like. In some embodiments, memory 88 stores program instructions that, when executed by processor 84, cause IMD 14 and processor 84 to perform the functions attributed to them herein.

Figure 6:
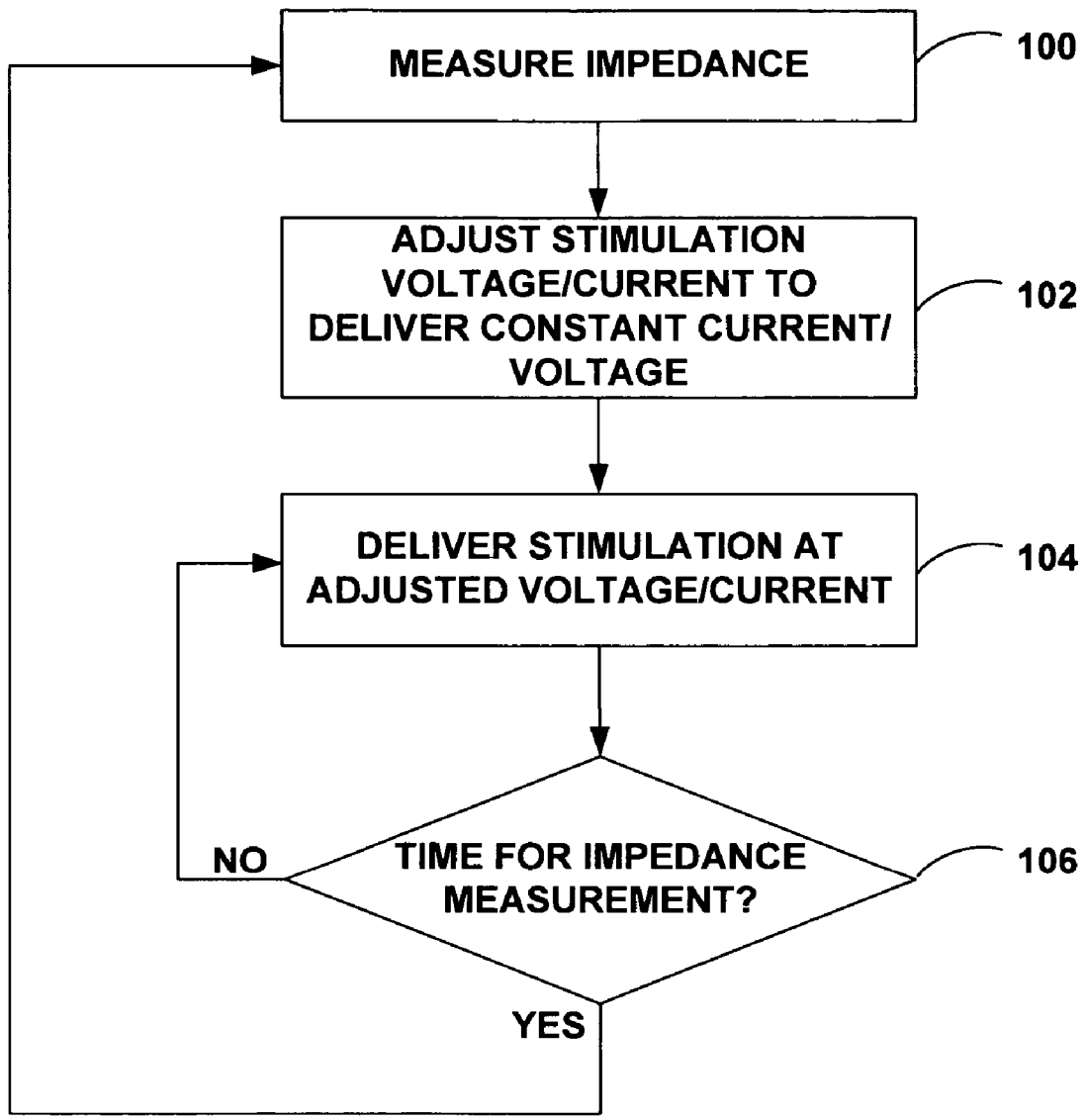
FIG. 6 is a flow diagram illustrating an example method for adjusting a stimulation voltage or current amplitude based on the impedance presented to a medical device.

FIG. 6 is a flow diagram illustrating an example method for adjusting a stimulation voltage or current amplitude based on a measurement of impedance presented to a medical device, which may be performed by a medical device, such as IMD 14. According to the method, IMD 14 and, more particularly, processor 84 of IMD 14 controls impedance measurement circuitry 90 to measure the impedance presented to stimulation circuitry 82 (100). Depending on whether IMD 14 is a constant voltage IMD directed to deliver constant current stimulation, or a constant current IMD directed to deliver constant voltage stimulation, processor 84 adjusts a stimulation voltage or current amplitude value provided to stimulation circuitry 82 based on the measured impedance in order to cause stimulation circuitry 82 to deliver stimulation with a substantially constant current or voltage amplitude (102).

Processor 84 controls stimulation circuitry 82 to deliver stimulation at the adjusted voltage or current amplitude value (104), until processor 84 determines that it is time for another impedance measurement (106).

Figure 7:
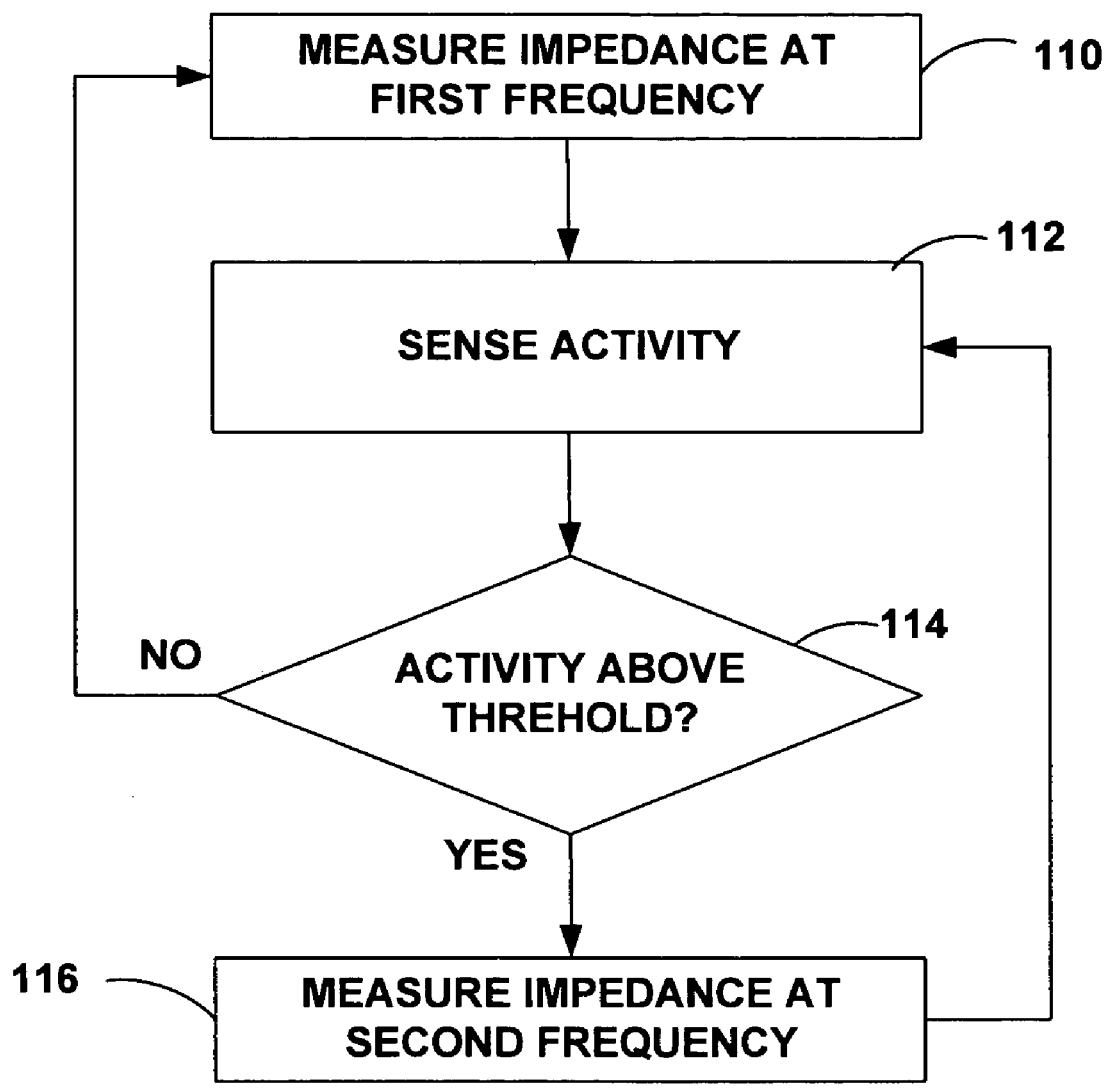
FIG. 7 is a flow diagram illustrating an example method for determining a presented impedance measurement frequency based on a sensed activity level.

FIG. 7 is a flow diagram illustrating a technique determining an impedance measurement frequency based on a sensed activity level, which may be performed by IMD 14. According to the example method, IMD 14 and, more particularly, processor 84 controls impedance measurement circuitry 90 to measure the impedance presented to stimulation circuitry at a first measurement frequency (110). Processor 84 also senses patient activity via activity sensor 92 (112). When processor 84 determines that the patient activity level is above a threshold value (114), processor 84 controls lead impedance measurements to occur at a second measurement frequency (116), until the activity level is no longer above the threshold. As discussed above, the first measurement frequency may be a lower frequency, such as on the order of hourly or daily measurements, while the second measurement frequency is a higher frequency, such as on the order of one measurement every one or more stimulation pulses.

The method of FIG. 7 illustrates an embodiment in which the relationship between patient activity and impedance measurement frequency is defined by two frequencies a threshold activity value. The invention is not so limited.

Figure 8A:
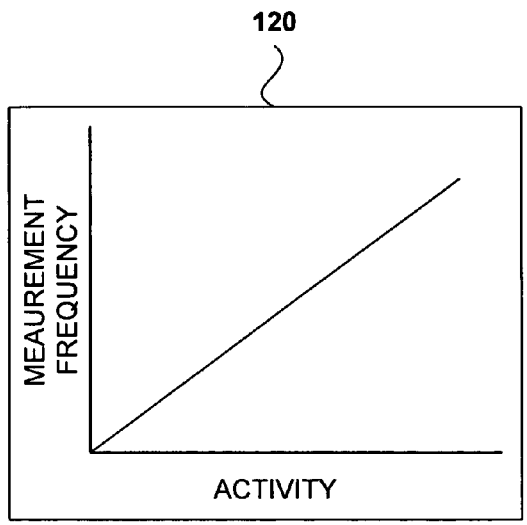
FIGS. 8A-8D are conceptual diagrams illustrating example relationships between patient activity and impedance measurement frequency.
Figure 8B:
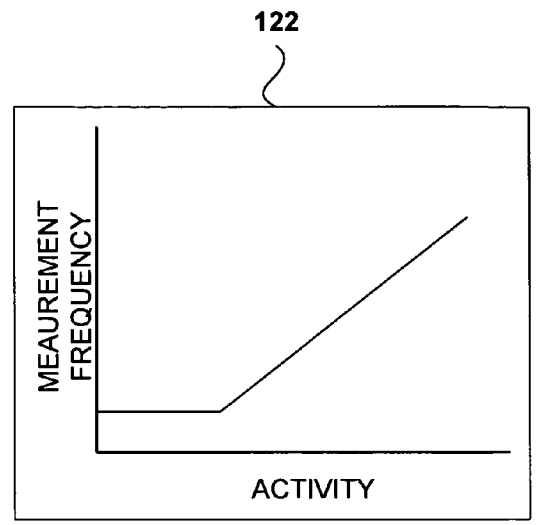
Figure 8C:
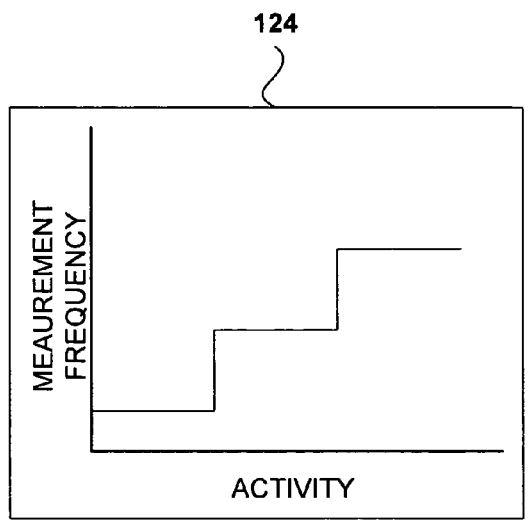
Figure 8D:
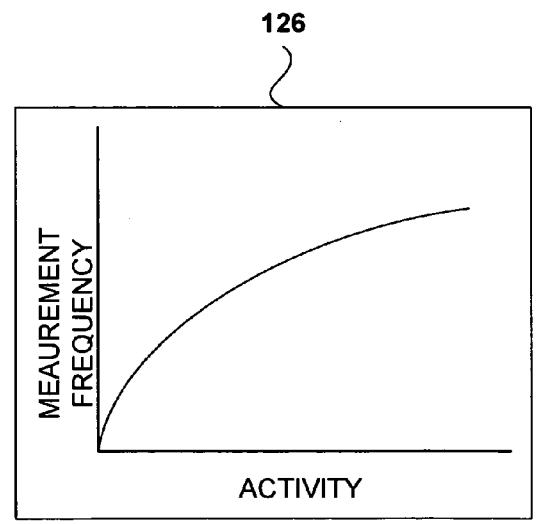

FIGS. 8A-8D are conceptual diagrams illustrating various additional example relationships 120-126 between patient activity and impedance measurement frequency. For example, FIG. 8A illustrates a linear relationship 120 between activity and frequency. FIG. 8B illustrates a relationship 122 in which impedance measurements occur at a nominal measurement frequency until a threshold activity level is reached, at which point the measurement frequency increases linearly with increased patient activity. FIG. 8C illustrates a relationship 124 characterized by a plurality of patient activity threshold values and measurement frequencies. FIG. 8D illustrates a logarithmic relationship 126 between measurement frequency and patient activity. It should be noted at that the relationships 120-126 depicted by FIGS. 8A-8D are only examples, and IMD 14 may store or be programmed to determine an impedance measurement frequency according to any function desired.

Many embodiments of the invention have been described. These and other embodiments are within the scope of the following claims.

The invention claimed is:

1. A programming device comprising:
a user interface; and
a processor that presents a user with an interface for selection of one of a constant current mode or a constant voltage mode via the user interface, receives a selection of one of the modes from the user via the user interface, configures a medical device according to the selected mode, and presents die user with either an interface for selection of a voltage amplitude or an interface for selection of a current amplitude via the user interface based on the selected mode,
wherein the processor configures the medical device to measure, using impedance measurement circuitry, an impedance presented to stimulation circuitry of the medical device based on the selected mode, and
wherein, when the medical device comprises constant voltage stimulation circuitry and the user selects the constant current mode, the processor configures the medical device to measure, using the impedance measurement circuitry, the presented impedance and adjust a stimulation voltage amplitude based on the measured impedance to deliver stimulation with a substantially constant current amplitude.

2. A programming device comprising:
a user interface; and
a processor that presents a user with an interface for selection of one of a constant current mode or a constant voltage mode via the user interface, receives a selection of one of the modes from the user via the user interface, configures a medical device according to the selected mode, and presents the user with either an interface for selection of a voltage amplitude or an interface for selection of a current amplitude via the user interface based on the selected mode,
wherein the processor configures the medical device to measure, using impedance measurement circuitry, an impedance presented to stimulation circuitry of the medical device based on the selected mode, and
wherein, when the medical device comprises constant current stimulation circuitry and the user selects the constant voltage mode, the processor configures the medical device to measure, using the impedance measurement circuitry, the presented impedance and adjust a stimulation current amplitude based on the measured impedance to deliver stimulation with a substantially constant voltage amplitude.

3. The programming device of claim 1, wherein the processor provides an impedance measurement frequency to the medical device.

4. A programming device comprising:
a user interface; and
a processor that presents a user with an interface for selection of one of a constant current mode or a constant voltage mode via the user interface receives a selection of one of the modes from the user via the user interface, configures a medical device according to the selected mode, and presents the user with either an interface for selection of a voltage amplitude or an interface for selection of a current amplitude via the user interface based on the selected mode,
wherein the processor configures the medical device to measure, using impedance measurement circuitry, an impedance presented to stimulation circuitry of the medical device based on the selected mode,
wherein the processor provides an impedance measurement frequency to the medical device, and
wherein the measurement frequency is variable as a function of patient activity measured by an activity sensor of the medical device, and the processor provides a relationship between the impedance measurement frequency and patient activity to the medical device.

5. A method comprising:
presenting a user with an interface for selection of one of a constant current mode or a constant voltage mode;
receiving a selection of one of the modes from the user;
configuring a medical device according to the selected mode; and
presenting the user with either an interface for selection of a voltage amplitude or an interface for selection of a current amplitude based on the selected mode,
wherein configuring the medical device comprises configuring the medical device to measure, using impedance measurement circuitry, an impedance presented to stimulation circuitry of the medical device based on the selected mode, and
wherein, when the medical device comprises constant voltage stimulation circuitry and the user selects the constant current mode, configuring the medical device comprises configuring the medical device to measure, using the impedance measurement circuitry, the presented impedance and adjust a stimulation voltage amplitude based on the measured impedance to deliver stimulation with a substantially constant current amplitude.

6. A method comprising:
presenting a user with an interface for selection of one of a constant current mode or a constant voltage mode;
receiving a selection of one of the modes from the user;
configuring a medical device according to the selected mode;
presenting the user with either an interface for selection of a voltage amplitude or an interface for selection of a current amplitude based on the selected mode,
wherein configuring the medical device comprises configuring the medical device to measure, using impedance measurement circuitry, an impedance presented to stimulation circuitry of the medical device based on the selected mode, and
wherein, when the medical device comprises constant current stimulation circuitry and the user selects the constant voltage mode, configuring the medical device comprises configuring the medical device to measure, using the impedance measurement circuitry, the presented impedance and adjust a stimulation current amplitude based on the measured impedance to deliver stimulation with a substantially constant voltage amplitude.

7. The method of claim 5, further comprising providing a measurement frequency to the medical device for measurement of the impedance.

8. A method comprising:
presenting a user with an interface for selection of one of a constant current mode or a constant voltage mode:
receiving a selection of one of the modes from the user;
configuring a medical device according to the selected mode, wherein configuring the medical device comprises configuring the medical device to measure, using impedance measurement circuitry, an impedance presented to stimulation circuitry of the medical device based on the selected mode;
presenting the user with either an interface for selection of a voltage amplitude or an interface for selection of a current amplitude based on the selected mode;
providing a measurement frequency to the medical device for measurement of the impedance,
measuring patient activity using an activity sensor of the medical device, wherein the measurement frequency of the impedance is variable as a function of patient activity, and providing a measurement frequency comprises providing a relationship between the measurement frequency of the impedance and patient activity.

9. A computer-readable medium comprising instructions that cause a programmable processor to:
present a user with an interface for selection of one of a constant current mode or a constant voltage mode;
receive a selection of one of the modes from the user;
configure a medical device according to the selected mode; and
present the user with either an interface for selection of a voltage amplitude or an interface for selection of a current amplitude based on the selected mode,
wherein the instructions that cause a programmable processor to configure the medical device comprise instructions that cause a programmable processor to configure the medical device to measure, using impedance measurement circuitry, an impedance presented to stimulation circuitry of the medical device based on the selected mode, and
wherein, when the medical device comprises constant voltage stimulation circuitry and the user selects the constant current mode, the instructions that cause a programmable processor to configure the medical device comprise instructions that cause a programmable processor to configure the medical device to measure, using the impedance measurement circuitry, the presented impedance and adjust a stimulation voltage amplitude based on the measured impedance to deliver stimulation with a substantially constant current amplitude.

10. A computer-readable medium comprising instructions that cause a programmable processor to:
present a user with an interface for selection of one of a constant current mode or a constant voltage mode;
receive a selection of one of the modes from the user;
configure a medical device according to the selected mode; and
present the user with either an interface for selection of a voltage amplitude or an interface for selection of a current amplitude based on the selected mode,
wherein the instructions tat cause a programmable processor to configure the medical device comprise instructions that cause a programmable processor to configure the medical device to measure, using impedance measurement circuitry, an impedance presented to stimulation circuitry of the medical device based on the selected mode, and
wherein, when the medical device comprises constant current stimulation circuitry and the user selects the constant voltage mode, the instructions that cause a programmable processor to configure the medical device comprise instructions that cause a programmable processor to configure the medical device to measure, using the impedance measurement circuitry, the presented impedance and adjust a stimulation current amplitude based on the measured impedance to deliver stimulation, with a substantially constant voltage amplitude.

11. The programming device of claim 2, wherein the processor provides an impedance measurement frequency to the medical device.

12. The method of claim 6, further comprising providing a measurement frequency to the medical device for measurement of the impedance.

* * * * *

UNITED STATES PATENT AND TRADEMARK OFFICE
CERTIFICATE OF CORRECTION

PATENT NO. : 7,389,147 B2
APPLICATION NO. : 11/119420
DATED : June 17, 2008
INVENTOR(S) : Wahlstrand et al.

It is certified that error appears in the above-identified patent and that said Letters Patent is hereby corrected as shown below:

Col. 9, Line 55: "presents die user" should read --presents the user--

Col. 10, Line 34: "interface receives" should read --interface, receives--

Col. 12, Line 33: "instructions tat cause" should read --instructions that cause--

Signed and Sealed this

Third Day of March, 2009

JOHN DOLL
*Acting Director of the United States Patent and Trademark Office*